(12) United States Patent
Wang et al.

(10) Patent No.: US 6,472,228 B2
(45) Date of Patent: Oct. 29, 2002

(54) COMPOSITION AND METHODS FOR SYNTHESIS OF NOVEL TRACERS FOR DETECTING AMPHETAMINE AND METHAMPHETAMINE IN SAMPLES

(75) Inventors: Guohong Wang; Thomas Foley, both of Rancho Cucamonga, CA (US)

(73) Assignee: Lifepoint, Inc., Rancho Cucamonga, CA (US)

(*) Notice: Subject to any disclaimer, the term of this patent is extended or adjusted under 35 U.S.C. 154(b) by 0 days.

(21) Appl. No.: 09/730,095

(22) Filed: Dec. 4, 2000

(65) Prior Publication Data

US 2002/0090661 A1 Jul. 11, 2002

(51) Int. Cl.$^7$ .................. G01N 33/532; G01N 33/533; G01N 33/545; C07D 209/04; C07D 311/82
(52) U.S. Cl. .................. 436/546; 435/7.93; 436/525; 436/526; 436/531; 436/534; 436/544; 436/546; 436/816; 548/455; 549/391
(58) Field of Search .................. 435/7.93; 436/531, 436/534, 544, 545, 546, 525, 816, 526; 548/455; 549/391

(56) References Cited

U.S. PATENT DOCUMENTS

| 5,183,740 A | 2/1993 | Ligler et al. |
| 6,020,209 A | 2/2000 | Narang et al. |

FOREIGN PATENT DOCUMENTS

| EP | 0279 213 B1 | 8/1988 |
| EP | 0371 253 A2 | 6/1990 |
| EP | 0375 422 A2 | 6/1990 |
| EP | 0386 644 A2 | 9/1990 |

OTHER PUBLICATIONS

R.D. Budd, Clinical Toxicology, 18(1), 91–110 (1981).*
Edwards, R., Radiolabelled Immunoassay, in *Principles and Practice of Immunoassay*, C.P. Price and D.J. Newman, Eds. Stockton Press, NY, NY, pp. 265–79, 1991.
March, J., *Advanced Organic Chemistry*, p. 531, New York: John Wiley & Sons, 4th Ed. (1992).
Nam, D. et al. Programme and Abstracts of TIAFT 2000 at Helsinki, 2000.
Liang, G., et al., Proc. of ICADTS 2000, Jun. 22–26, 2000.
Mujumdar, R.B., et al., Bioconjugate Chemistry, vol. 4, p. 105 (1992).
"Saliva as a Diagnostic Fluid," Ed by D. Malamud and L. Tabak, Annals of the New York Academy of Sciences, 1993, v. 694.
Hao Yu et al., "Use of the USDT Flow Immunosensor for Quantitation of Benzolecgonine in Urine." *Biosensors and Bioelectronics*. 1991: 11(8):725–734.

G.J. Turner, D.L. Colbert, and B.Z. Chowdry, "A Broad Spectrum Immunoassay Using Fluorescence Polarization for the Detection of Amphetamines in Urine." *Ann. Clin. Biochem.* 1991: 28:588–594.
Li M et al., "Amine–Reactive Forms of a Luminescent Diethylenetriaminepentaacetic Acid Chelate of Terbium and Europium: Attachment to DNA and Energy Transfer Measurements." *Bioconjugate Chem.* 1997; 8: 127 at FN 1.
Nagaraj S et al., "Visible Diode Laser Induced Fluorescence Detection for Capillary Electrophoretic Analysis of Amantadine in Human Plasma following Precolumn Derivatization with Cy5.29.OSu." *J. Pharm. Biomed. Anal.* 1998; 18(3): 411–420.
United States Environmental Protection Agency, Office of Pollution Prevention and Toxics, "Ethylenediamine (CAS Reg. No. 107–15–3) Proposed Acute Exposure Guideline Levels (AEGLs)" *Public Draft*, Federal Register–May 2000. Available at http://www.epa.gov/fedrgstr/EPA–TOX/2000/June/Day–23/4878.pdf. Accessed Mar. 19, 2002.
Vapatalo, H. K. S, and Senius, K. E., "Comparison of Saliva and Urine Samples in Thin–Layer Chromatographic Detection of Central Nervous System Stimulants." *Intl. J. Clin. Pharmacol. Res.* 1984; 4: 5–8.
R.P. Haugland, Molecular Probes, Handbook of Fluorescent Probes and Research Chemicals, 5th Ed., Molecular Probes, Inc., Eugene, Oregon, 1992.
Cook, C. E., et al., "Pharmacokinetics of Methamphetamine Self–Administered to Human Subjects by Smoking s–(+)–Methamphetamine Hydrochloride." *Drug Metab. Dispos.* 1996; 21: 717–723.
Suzuki, S., et al., "Analysis of Methamphetamine in Hair, Nail, Sweat, and Saliva by Mass Fragmentography." *J Anal. Toxicol.* 1989; 13: 176–178.
K. Peter C. Vollhardt, *Organic Chemistry*, pp. 191–92, New York: W.H. Freeman and Company; 1987.
P. Mason et al, J. Immunoassay, 4(1), 83–98 (1983).*

* cited by examiner

Primary Examiner—Mary E. Ceperley
(74) Attorney, Agent, or Firm—Lyon & Lyon LLP

(57) ABSTRACT

This invention relates to novel tracers and their synthesis and use in an immunoassay for the detection of controlled drugs such as amphetamine (APM), methamphetamine (MAPM) and their derivatives, in a biological or aqueous sample. In particular, this invention provides methods for synthesizing novel tracers in which a non-controlled substance is both the starting material in tracer synthesis and the binding site on the resulting novel tracer for the antibody, thereby eliminating the necessity of using controlled substances as starting materials. In addition, the novel tracers of the present invention can be used as an analyte analog in an immunoassay, such as a continuous flow displacement immunoassay. It was unexpectedly discovered that the novel tracers of the present invention substantially improve the performance of the continuous flow displacement immunoassay as compared with conventionally designed tracers.

28 Claims, 7 Drawing Sheets

Fig. 1 Synthetic Routes to Immunoassay Tracers (* a label)

Amphetamine (n=1)     Methamphetamine (n=1)

Fig. 12. General procedures for preparation of p', m' and o'-substituted amphetamines tracers:
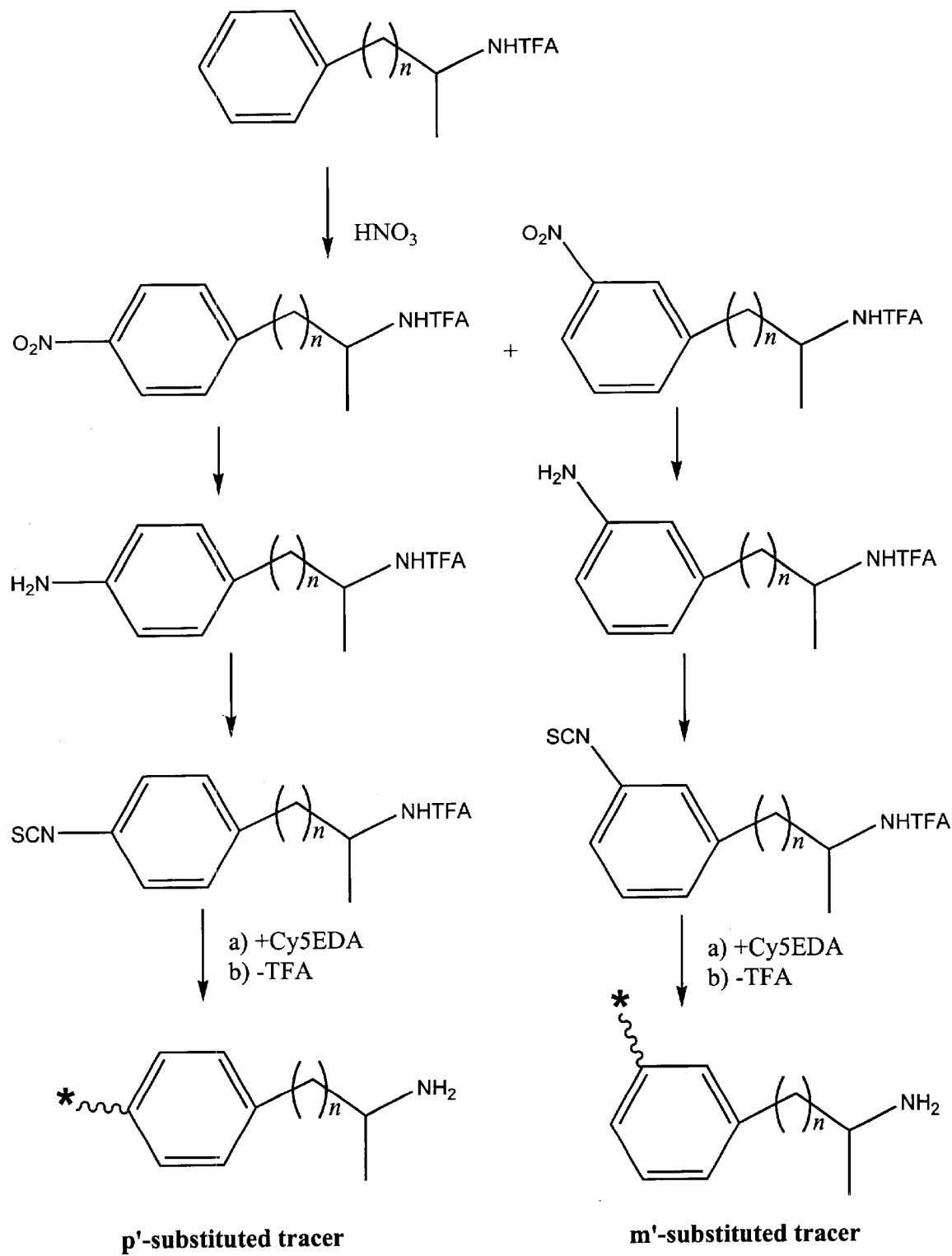

Fig. 13 Synthesis of one of the preferred tracers:
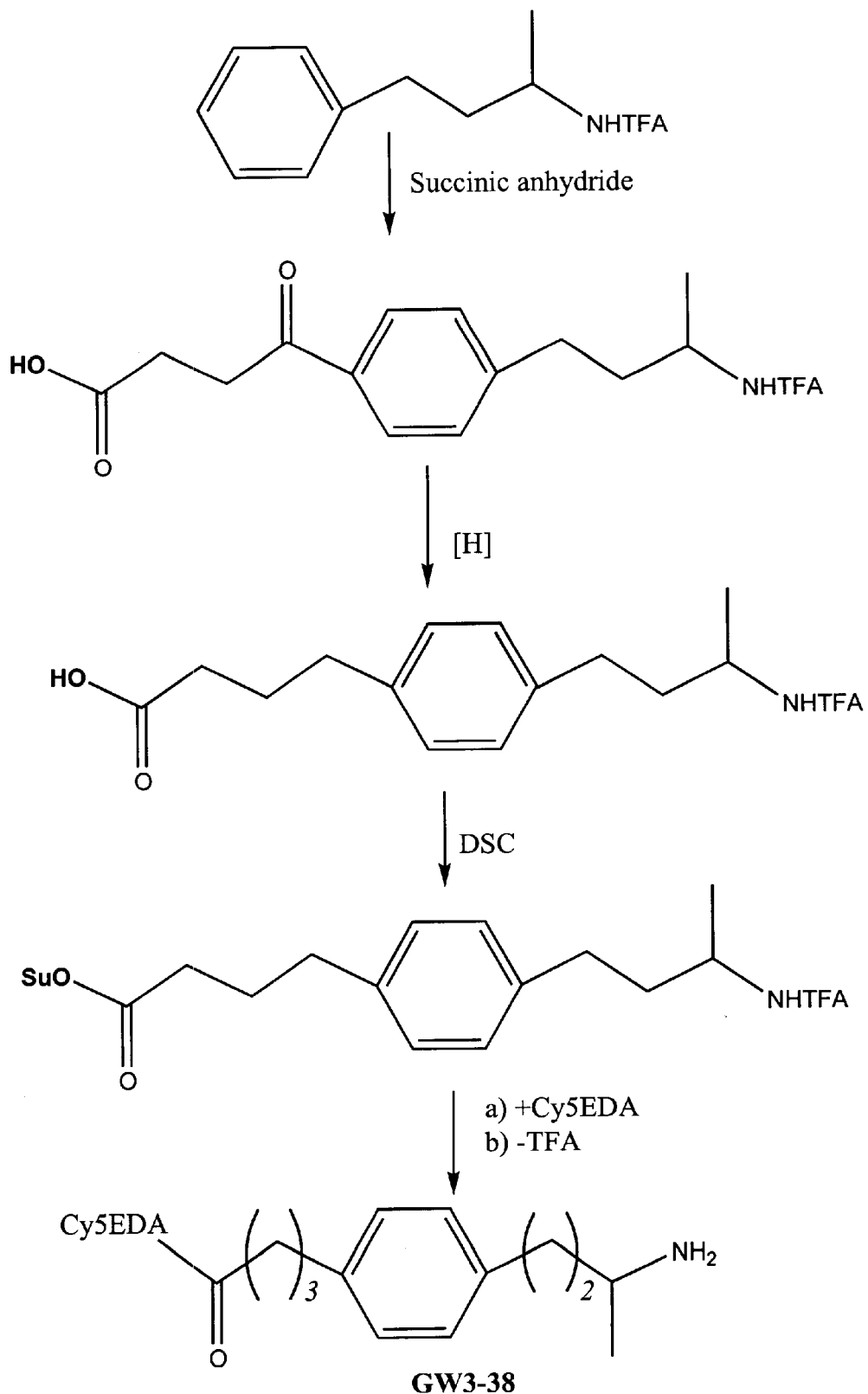

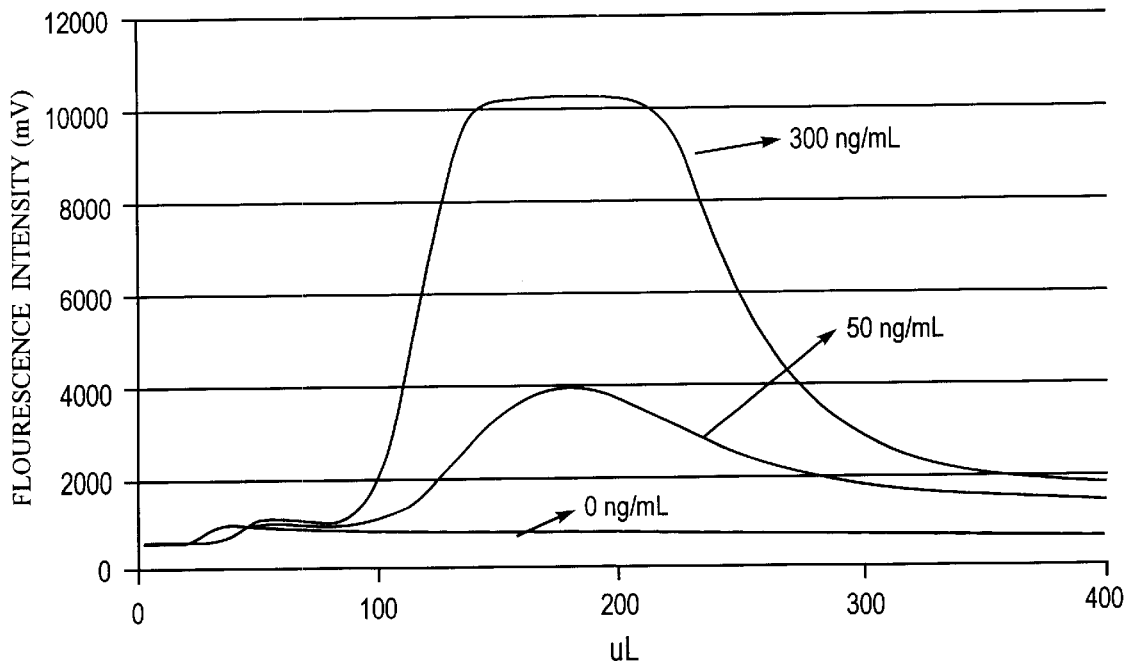
Fig. 14  FLOW IMMUNOASSAY OF AMPHETAMINE WITH PREFERRED NON-DRUG-BASED TRACER IN FIG. 9
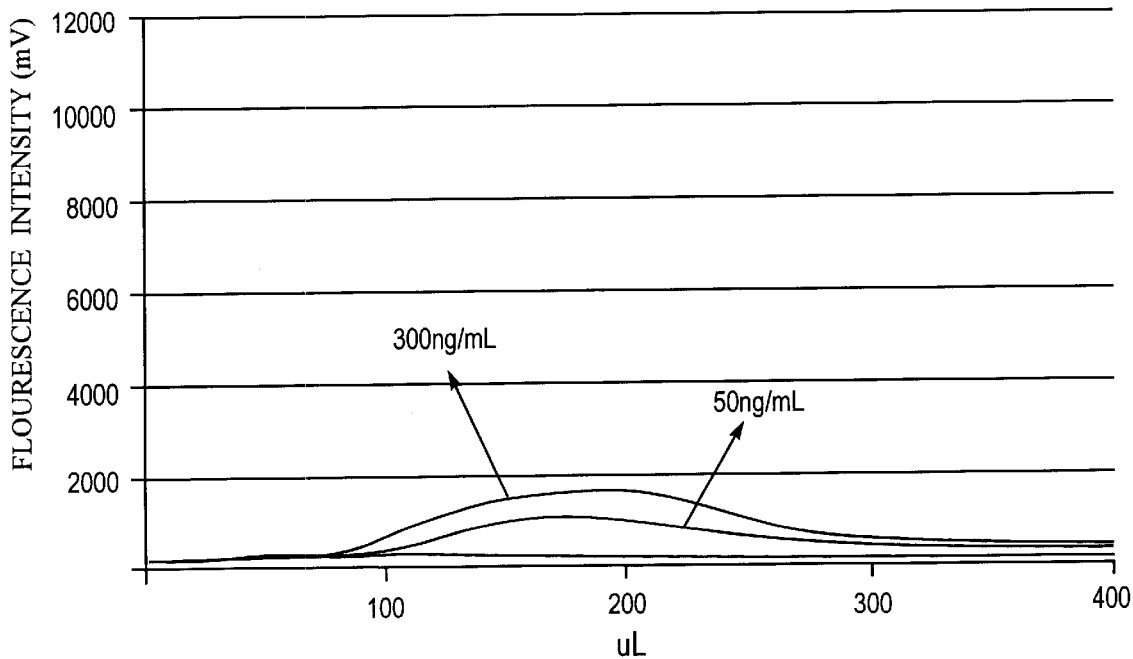
Fig. 15  FLOW IMMUNOASSAY OF AMPHETAMINE WITH CONVENTIONAL DRUG-BASE TRACER IN FIG. 11

COMPOSITION AND METHODS FOR SYNTHESIS OF NOVEL TRACERS FOR DETECTING AMPHETAMINE AND METHAMPHETAMINE IN SAMPLES

FIELD OF INVENTION

This invention relates to novel tracers and their synthesis and use in an immunoassay for the detection of controlled drugs such as amphetamine (APM), methamphetamine (MAPM) and their derivatives, in a biological or aqueous sample. In particular, this invention provides methods for synthesizing novel tracers in which a non-controlled substance is both the starting material in tracer synthesis and the binding site on the resulting novel tracer for the antibody, thereby eliminating the necessity of using controlled substances as starting materials. In addition, the novel tracers of the present invention can be used as an analyte analog in an immunoassay, such as a continuous flow displacement immunoassay. A continuous flow displacement immunoassay works on a principle whereby immobilized antibody is first saturated with a labeled analyte analog, the labeled analyte analog is displaced by the analyte in the testing sample, and the displaced labeled analyte analog is then measured. It was unexpectedly discovered that the novel tracers of the present invention substantially improve the performance of the continuous flow displacement immunoassay as compared with conventionally designed tracers.

BACKGROUND OF THE INVENTION

Amphetamine and methamphetamine are derivatives of a compound known as a phenylethylamine. Both amphetamine and methamphetamine are stimulants of the central nervous system and of the sympathetic division of the peripheral nervous system. Like other stimulants, the short-term effects of amphetamine or methamphetamine intake include increased heart rate, increased blood pressure, reduced appetite, dilation of the pupils, feelings of happiness and power, and reduced fatigue. It is because of their stimulant effects that these compounds are abused and sold illicitly.

Due to common abuse of amphetamines and methamphetamines, there is a growing need for non-invasive, rapid tests to detect the presence of these drugs in biological specimens. In the past, amphetamines in biological samples were detected by a number of techniques such as thin layer chromatography (TLC), high pressure liquid chromatography (HPLC), and gas chromatography/mass spectrometry (GC/MS). These assays are generally time consuming and have poor assay sensitivity. See Vapatalo, H. K. S, and Senius, K. E., Comparison of Saliva and Urine Samples in Thin-Layer Chromatographic Detection of Central Nervous System Stimulants, Intl. J. Clin. Pharmacol. Res., 4: 5–8 (1984), Cook, C. E., et al., Pharmacokinetics of Methamphetamine Self-administered to Human Subjects by Smoking s-(+)-Methamphetamine hydrochloride, Drug Metab. Dispos., 21: 717–723 (1993), Suzuki, S., et al., Analysis of Methamphetamine in Hair, Nail, Sweat, and Saliva by Mass Fragmentography, J. Anal. Toxicol., 13: 176–178 (1989), which are incorporated herein by reference as if fully set forth. In addition, they are difficult in that highly trained personnel are required to perform TLC, HPLC and GC/MS assays. Immunoassays have provided preferable alternative methods to using TLC, HPLC and GC/MS assays for the detection and quantitation of amphetamines and methamphetamines. In particular, immunoassays have improved sensitivity, efficiency and are less labor intensive. A number of immunoassay techniques for detecting amphetamines and methamphetamines in urine have been developed. See Brynes, et. al. EPO #279,213 B1, Hu et. al., EPO #371, 422A2, and Helman et. al., EPO #371,253 A2 which are incorporated herein by reference as if fully set forth. Further, the continuous flow displacement immunoassay has been demonstrated as a useful and rapid method for detecting drugs of abuse in saliva and urine. See Hao Yu et al., Use of the USDT Flow Immunosensor for Quantitation of Benzolecgonine in Urine, Biosensors and Bioelectronics, 725–734 (1996); Nam, D. et al. Programme and Abstracts of TIAFT 2000 at Helsinki, 2000; Liang, G., et al., Proc. of ICADTS 2000, Jun. 22–26, 2000, which are incorporated herein by reference as if fully set forth.

A tracer as used herein is a labeled antigen or hapten used in an immunoassay to compete with the particular substance of interest (the analyte) for antigen binding sites of an antibody. The tracer can be a labeled antigen or hapten identical to the analyte to be detected, or it can be modified in such a way that it is structurally related to the analyte and has the desired cross-reactivity toward the selected antibody. In a continuous flow displacement immunoassay for example, a modification to the labeled antigen or hapten that decreases binding affinity may actually enhance the displacement reaction, and consequently the sensitivity of the system. For detection of illicit drugs, most immunoassays generally used the illicit drugs themselves, i.e. labeled amphetamines and methamphetamines, as tracers to detect the presence and or quantity of these substances in the sample. Because these drugs are illegal, a series of procedural guidelines and paperwork accompanies their utilization in the laboratory. Recent use of non-controlled substances as starting materials in amphetamine and methamphetamine tracer synthesis has been reported (Heiman, D., et al. EP 0 371 233 A2), but the final tracer synthesized still contains the amphetamine molecule itself as the binding site for the anti-amphetamine antibodies.

As shown in FIG. 1, there are different ways of synthesizing tracers. One of the common methods of tracer synthesis involves using the illicit drugs, such as amphetamines and methamphetamines, as the starting materials. (Salamamone, S. et al, EP 0 386 644 A2) These starting materials are carried through multiple synthesis steps to yield a drug-based tracer. (See FIG. 1, Method A.) Another alternative method of synthesizing tracers involves the use of non-controlled substances as starting materials to yield a drug-based tracer. (Heiman, D. F. et al., EP 0 371 233 A2) (See FIG. 1, Method B.) In both these methods, the synthesis routes involve the illicit drugs as starting materials, intermediates or final prepared tracer.

The present invention provides methods for the synthesis of a novel set of tracers produced from non-controlled substances yielding a labeled non-controlled substance as the tracer (See FIG. 1, Method C). The synthesis of these non-drug based tracers does not involve the production of illicit drugs at any point in the synthesis process. We have found that these novel tracers are ideal for use in immunoassays detecting the presence and/or quantity of amphetamines and methamphetamines in biological or aqueous samples. We have found that it is not necessary to have the specific labeled analyte itself (i.e., amphetamine) as the tracer as long as the antibody in the immunoassay system binds to the tracer with a decreased affinity from that of the analyte in the biological samples. The novel tracers of the present invention are particularly useful in the continuous flow displacement immunoassay.

SUMMARY OF THE INVENTION

This invention relates to novel compositions suitable for use in immunoassays for detecting amphetamine (APM), methamphetamine (MAPM) and their derivatives in biological or aqueous samples. The tracer synthesis methods developed in this invention eliminate the use of the illicit drugs, i.e. amphetamine and methamphetamine, as the starting materials for or products of tracer synthesis. These non-drug based tracers are particularly useful for the continuous flow displacement immunoassay. The present invention describes the processes for synthesizing the novel tracers, and the application of these tracers in fluorescence immunoassays for the detection and quantitation of phenylethylamine derivatives in biological samples.

FIG. 2 depicts the basic structures of amphetamine and methamphetamine. Amphetamine and methamphetamine are examples of the analytes that can be detected in the immunoassays of the present invention. Amphetamine has an n value of 1. The tracers of this invention have the n value of greater than 1. The preferred tracers have an n value that is 2 or more. Thus, in one embodiment of the invention, a synthetic tracer is provided that comprises a phenylalkylamine of the formula selected from the group consisting of:

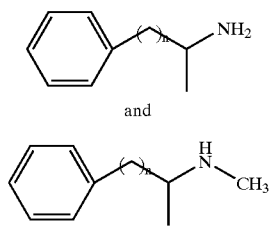

attached to a label, wherein n>1. FIGS. 3 and 4 show common fluorescent labels that can be used in the tracer synthesis of this invention.

In one embodiment of the present invention, the synthetic novel tracer is the compound, labeled 1-methyl-3-phenylalkylamine, which is depicted in FIG. 5.

In another embodiment of the present invention, the synthetic novel tracer is the compound N-labeled 1-methyl-3-phenylalkylamine, which is depicted in FIG. 6.

In another embodiment of the present invention, the synthetic novel tracer is a compound labeled N-methyl-1-methyl-3-phenylalkylamine, which is depicted in FIG. 7.

In another embodiment of the present invention, the synthetic novel tracer is a compound N-labeled N-methyl-1-methyl-3-phenylalkylamine, which is depicted in FIG. 8.

In a preferred embodiment of the present invention, the synthetic novel tracer is the reaction product of succinidyl active ester of para-hemisuccinito-1-methyl-3-phenylpropylamine-N-trifluoroacetamid with Cy5EDA shown in FIGS. 9 and 10. The preferred tracer is synthesized by the method described in Example II.

BRIEF DESCRIPTION OF THE DRAWINGS

FIG. 12 is a flow-chart setting forth the general procedures for preparation of p', m' and o'-substituted amphetamine tracers.

FIG. 13 is a flow-chart setting forth the procedure for synthesis of one of the preferred tracers of the present invention.

FIGS. 14 and 15 show the comparison of the flow immunoassay of amphetamine with the preferred tracer GW3-38 and the conventional tracer GW5-12.

DETAILED DESCRIPTION OF THE PREFERRED EMBODIMENTS

Figure 1:
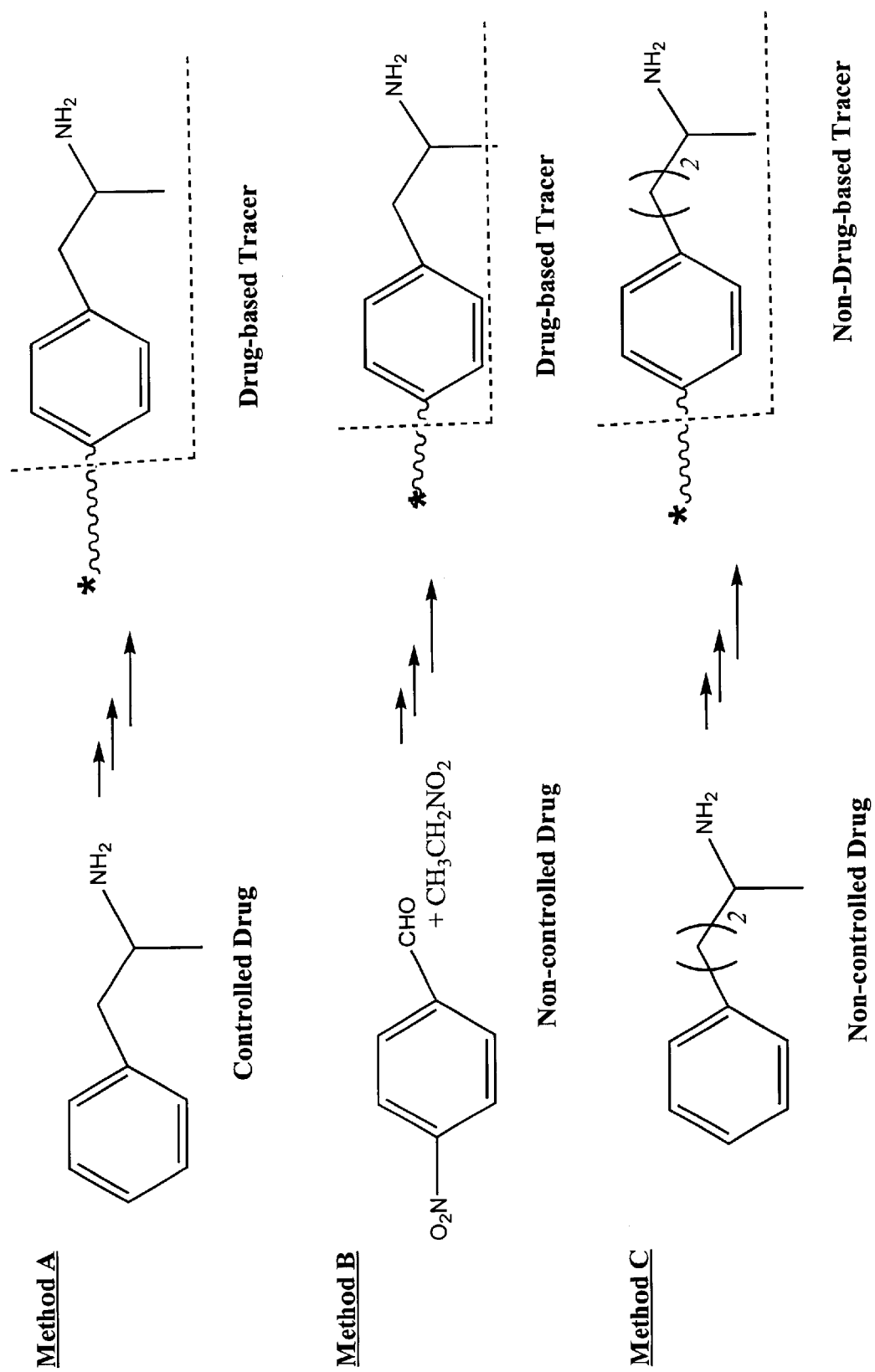
FIG. 1 shows methods of tracer preparation. Method A involves the use of illicit drugs as starting materials to yield a drug-based tracer. Method B involves the use of non-controlled substances to yield a drug-based tracer. Method C discloses the method of the present invention of tracer synthesis using non-controlled substances as starting materials and yielding a non-drug-based tracer.
Figure 2:
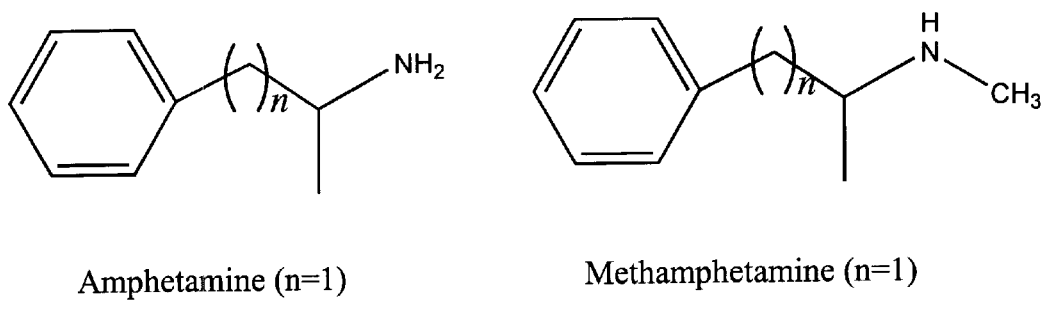
FIG. 2 shows the basic structures of amphetamine and methamphetamine.
Figure 3:
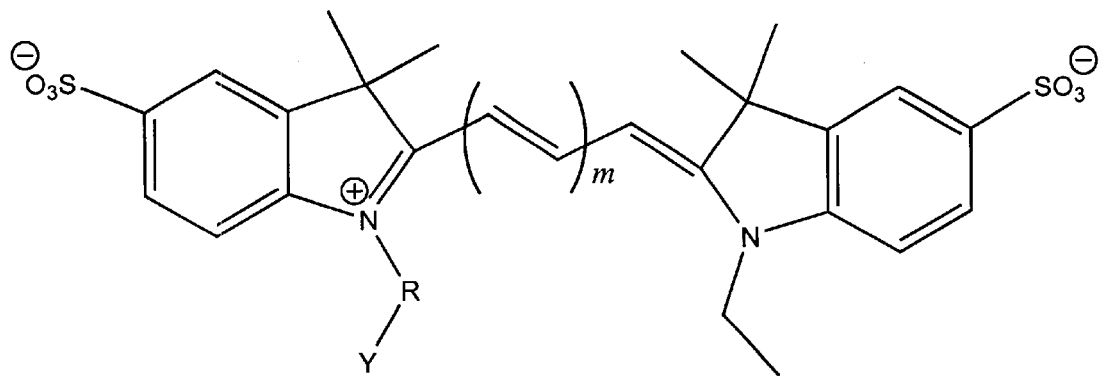
FIGS. 3 and 4 show common fluorescent labels that can be used in the tracer preparation of this invention.
Figure 4:
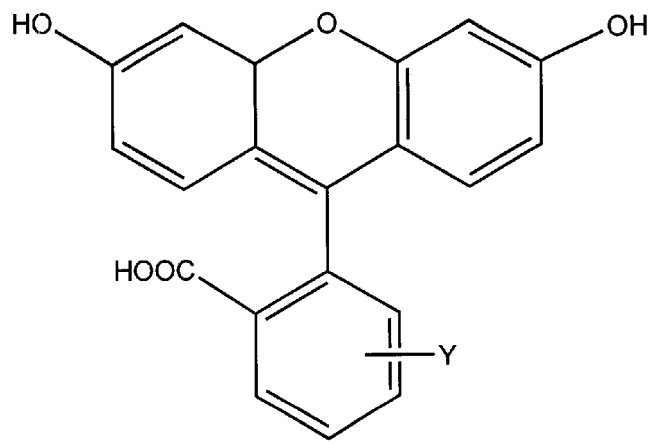
Figure 5:
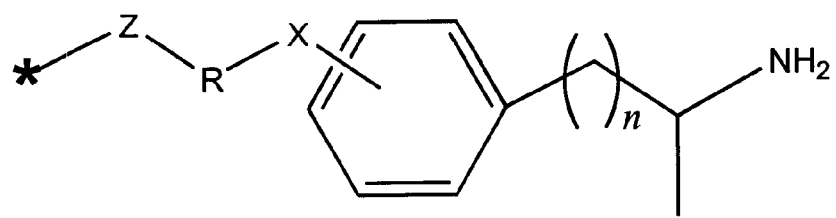
FIG. 5 depicts the synthetic novel tracer compound N-labeled 1-methyl-3-phenylalkylylamine.
Figure 6:
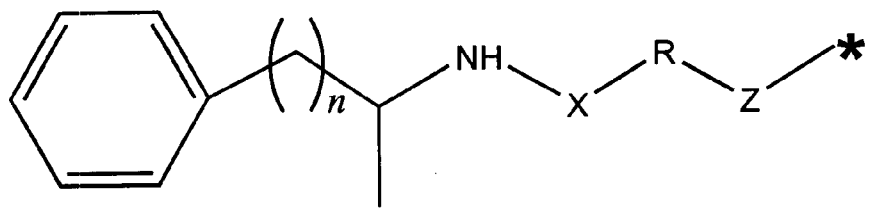
FIG. 6 depicts the synthetic novel tracer compound labeled 1-methyl-3-phenylalkylamine.
Figure 7:
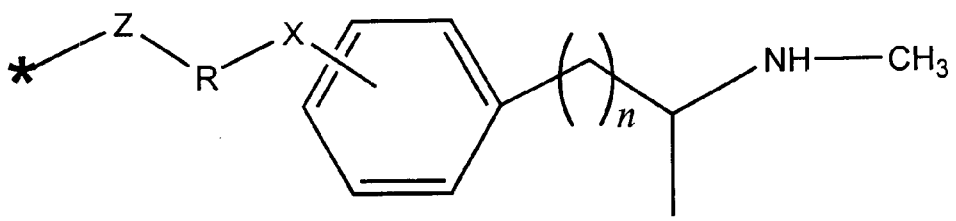
FIG. 7 depicts the synthetic novel tracer compound labeled N-methyl-1-methyl-3-phenylalkylamine.
Figure 8:
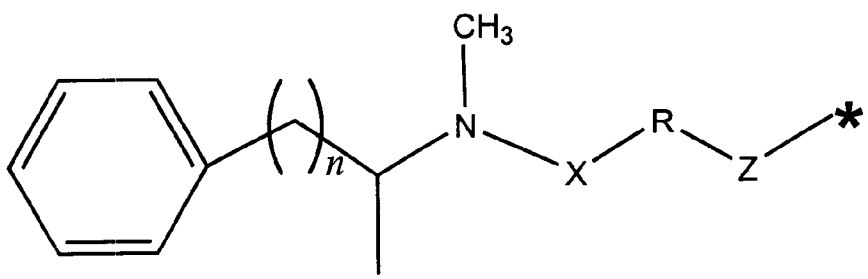
FIG. 8 depicts the synthetic novel tracer compound N-labeled N-methyl-1-methyl-3-phenylalkylamine.

This invention provides compositions and methods for synthesizing compounds for use in fluorescence immunoassays for detecting the presence and or quantity of amphetamine, methamphetamine and their derivatives in biological samples. The compositions or tracers for the detection of amphetamine and methamphetamines in biological samples are especially suitable for continuous flow displacement immunoassays.

In continuous flow displacement immunoassays, the kinetic properties of the analyte and the antibody play a very important role. An analyte is the substance being tested in an immunoassay. For instance, in the present invention, the analyte can be amphetamine or methamphetamine. An antibody recognizes and is capable of specifically binding to the analyte. A tracer is a labeled compound that competes with the analyte for binding to the antibody. The present invention uses a tracer that has three parts, namely, a site that binds to an antibody, a linking group, and a label. The site on the analyte that binds to the antibody is usually similar to the site on the tracer that binds to the antibody. In other words, if the analyte is amphetamine, the antibody to amphetamine recognizes the same binding site on the tracer that it recognizes on the analyte.

A typical continuous flow displacement immunoassay involves a solid-phase immobilized antibody to amphetamine or methamphetamine. The antigen binding site of the antibody is exposed to a synthetic labeled tracer to form a labeled synthetic tracer-antibody complex. The antibody is exposed to tracers such that the antigen binding sites of the antibody are saturated with the labeled synthetic tracers. Next, a biological sample suspected of containing the analyte, amphetamine or methamphetamine, is continuously flowed past the solid-phase immobilized antibody-labeled synthetic tracer complex. If analyte is present in the sample, the analyte binds to the antibody and displaces the labeled synthetic tracer. Detection of the labeled tracer downstream from the binding point hence shows the presence and or quantity of the analyte present in the biological sample. See Ligler, et al., U.S. Pat. No. 5,183,740, which is incorporated herein by reference as if fully set forth.

The success of developing a continuous flow displacement immunoassay based product, is based on the selection of antibody and tracer to achieve a fast dissociation rate of the bound tracer from the antibody, thereby permitting a rapid binding of the analyte. In general, the ideal continuous flow displacement immunoassay utilizes a system where the antibody has a high affinity for the analyte, and a lower affinity for the tracer. This arrangement where the antibody has a high affinity for the analyte and a lower affinity for the tracer promotes faster displacement. In the present invention, the tracers embody the following characteristic: the affinity of the tracer for the antibody is anywhere between 20–100%. A preferred tracer has about 40–80% cross-reactivity for the antibody. For the purposes of this invention, it is immaterial that the tracer be structurally related to the analyte, amphetamine or methamphetamine. So long as the ligand-binding site of the tracer has 20–100% cross-reactivity with the antibody, it is suitable for use in an immunoassay, especially, the continuous flow displacement immunoassay. Most antibodies to amphetamine and methamphetamine recognize the phenylethylamine derivatives. The present tracers are useful, so long as the antibodies are capable of recognizing the phenylethylamine analogs. Structural similarity to the analyte is not at issue. This characteristic, the structural dissimilarity between the tracer and the analyte, distinguishes the present tracers from those of prior art.

Labeling of the tracer may be carried out by means of conventional methods well known in the art. The label itself may suitably be a fluorophore, a chromophore, a radiolabel, a metal colloid, an enzyme, or a chemiluminescent or bioluminescent molecule. Suitable fluorophores and chromophores are disclosed in R. P. Haugland, Molecular Probes, Handbook of Fluorescent Probes and Research Chemicals, 5$^{th}$ Ed., Molecular Probes, Inc., Eugene, Oreg., 1992, which is incorporated herein by reference. Examples of preferred fluorophores include fluorescein, rodamine, and sulfoindocyanine dye Cy5 (Mujumdar, R. B., et al., Bioconjugate Chemistry, vol. 4, p. 105 (1992).

An extensive range of antibodies applicable for use in this invention are commercially available (for example, from Omega Biologicals, Inc., 910 Technology Blvd., Bozeman, Mont.) or can be made from descriptions of methods of preparation available in the literature. Any antibodies, such as monoclonal or polyclonal antibodies, which are commercially available or described in the literature can be employed or adapted to the method of this invention for identification of a wide range of targets.

The method can be used to detect specific components of biological or aqueous samples, including but not limited to water, blood, plasma, serum, blood or urine. Saliva has been demonstrated as a useful test matrix for the detection and measurement of drugs of abuse. ("Saliva as a Diagnostic Fluid", Ed by D. Malamud and L. Tabak, Annals of the New York Academy of Sciences, 1993, V. 694.) For example, methamphetamine in saliva samples can be detected by GC/MASS up to 2 days after the last dose. (S. Suzuki, T. Inoue and S. Inayama, Analysis of methamphetamine in hair, nail, sweat, and saliva by mass fragmentography, J. Anal. Toxicol. 1989,13, 176–178.)

The following examples are giving to illustrate the specific applications of the present invention including specific techniques which can be used to perform the invention. These specific examples are not intended to limit the scope of the invention described in the application.

EXAMPLE I

General Procedure for Preparation of Labeled Tracer

A flow-chart for the synthesis of a p', o' and m'-substituted tracers is set forth in FIG. 12. A detailed description of the steps for preparation follows.

A. Preparation and Isolation of para, meta, and ortho-nitroamphetamine-N-trifluoroacetamide.

0.7 mL of trifluoroacetic anhydride was added slowly to a solution of a mixture of 0.4 g of para-, meta-, and ortho-nitroamphetamine in 1 mL of acetronitrile at 0C. The resulting mixture was stirred at 0° C. for one hour, and was kept in the refrigerator at 4° C. overnight. The volatile material was removed and the crude product was purified with a silica gel column and eluted with 1:2 Ethyl acetate/hexane. In this manner, 0.15 g of a pure para-nitroamphetamine-N-trifluoroacetamide, 0.03 g of a pure meta-nitroamphetamine-N-trifluoroacetamide, and 0.04 g of a pure ortho-nitroamphetamine-N-trifluoroacetamide was obtained.

B. Preparation of para-aminoamphetamine-N-trifluoroacetamide:

0.15 g of prepared para-nitroamphetamine-N-trifluoroacetamide was dissolved in 8 ml of Ethanol. 0.4 mg of 10% Pd/C was added to the solution. The mixture was hydrogenated under $H_2$ at room temperature overnight. The catalyst and solvent were removed, leaving a dark green residue. The resulting mixture was purified by preparative silica thin layer chromatography, using a 1/1 mix of Ethyl acetate/Hexane as a developing solvent. 0.75 mg of the corresponding amine product was thus obtained.

C. Preparation of para-isothiocyanatoamphetamine-N-trifluoroacetamide:

A mixture of 25 mg of para-aminoamphetamine-N-trifluoroacetamide in 0.5 ml of dichloromethane was stirred, and 15 μl of $NaHCO_3$ and thiophosgene were added to the mixture. The resulting mix was stirred at room temperature for 30 minutes. The reaction mixture was next purified with a silica plate, giving 21 mg of para-isothiocyanantoamphetamine-N-trifluroacetamide.

D. Coupling of para-isocyanatoamphetamine-N-trifluoroacetamide with Cy5EDA:

A mixture of 2 mg of para-isothiocyanatoamphetamine-N-trifluoroacetamide and Cy5EDA in 0.5 ml of borate buffer (pH 8) was stirred at room temperature for four hours. The resulting solution was directly spotted onto a C18 plate, and developed with 70/30 (v/v) Methanol/Water. The product band was cut out and extracted with methanol.

EXAMPLE II

Preparation of a Preferred Amphetamine Immunoassay Tracer

A flow-chart for the synthesis of a preferred tracer is set forth in FIG. 13. A detailed description of the steps for preparation of the tracer follows.

Step 1: Preparation of 1-methyl-3-phenylpropylamine-N-trifluoroacetamide:

A solution of 3 g of 1-methyl-3-phenylpropylamine in 5 ml of acetronile was stirred at room temperature. 4 mL of trifluoroacetic anhydride and 1.3 mL of pyridine were added to the solution at room temperature. The resulting reaction mixture was stirred at room temperature overnight, and the mixture was then placed in ice water. The crude product was extracted with ethyl acetate, and the combined organic layers were dried over $Na_2SO_4$. Removal of the organic solvent yielded 1-methyl-3-phenylpropylamine-N-trifluroacetamide.

Step 2: Preparation ofpara-hemisuccinito-1-methyl-3-phenylpropylamine-N-trifluoroacetamide $AlCl_3$ was added to a mixture of 0.24 g succinic anhydride and 0.4 g 1-methyl-3-phenylpropylamine-N-trifluoroacetamide in 5 mL of dichloromethane at room temperature. The resulting mixture was stirred at 0° C. for one hour and then left at room temperature overnight. 5 ml of 3M aqueous HCl solution was added to the mixture and the organic layers were extracted with ethyl acetate. The combined organic layers were dried over $Na_2SO_4$, and yielded a crude product of 0.5 g. Further purification of the crude product was completed with a silica gel column, eluting with 1:2 ethyl/hexanes. 0.3 g of pure para-hemisuccinito-1-methyl-3-phenylpropylamine-N-trifluoroacetamide was obtained.

Step 3: Reduction of para-hemisuccinito-1-methyl-3-phenylpropylamine-N-trifluoroacetamide 0.2 g of the prepared para-hemisuccinito-1-methyl-3-phenylpropylamine-N-trifluroacetamide was dissolved in 3 ml of acetic acid. 0.3 mg of 10% Pd/C was added to the solution. The mixture was hydrogenated under $H_2$ at room temperature overnight, and the catalyst and solvent were removed, leaving an oily residue. The resulting mixture was purified by preparative silica TLC, using ethyl acetate/hexane as a developing solvent in a ratio of 1:1. 83 mg of pure reduced para-hemisuccinito-1-methyl-3-phenylpropylamine-N-trifluroacetamide was thus obtained.

Step 4: Preparation of succinimidyl active ester of para-hemisuccinito-1-methvl-3-phenylpropylamine-N-trifluroacetamide 40 mg of N,N'-disuccinmidyl carbonate and 60 1l of pyridine was added to a stirred mixture of 40 mg para-hemisuccinito-1-methyl-3-phenylpropylamine-N-trifluoroacetamide in 1 mL of acetonitrile. The resulting mixture was stirred at room temperature for 4 hours. Purification of the reaction mixture with a silica plate gave 25 mg of succinimidyl active ester of para-hemisuccinito-1-methyl-3-phenylpropylamine-N-trifluroacetamide.

Step 5: Coupling of succinimidyl active ester of para-hemisuccinito-1-methyl-3-phenvlpropylamine-N-trifluoroacetamide with Cy5EDA A mixture of 2 mg of succinimidyl active ester of para-hemisuccinito-1-methyl-3-phenylpropylamine-N-trifluoroacetamide and 2.5 mg of Cy5EDA in 0.5 ml of borate buffer (pH 9) was stirred at room temperature for 4 hours. The resulting solution was purified with a C18 plate, and developed with methanol and water in a ratio of 70/30 (v/v). The product band was cut and extracted with methanol. The coupled product is the preferred amphetamine immunoassay tracer.

EXAMPLE III

Flow Immunoassay Procedure

LifePoint, Inc. developed the Flow Immunoassay Instrument which contains the necessary pumps, valves, tubing, exchangeable columns and fluorescence detector for performing a continuous flow displacement immunoassay. Amphetamine standards were prepared by adding amphetamine (Sigma Chemicals, St. Louis, Mo.) at different concentrations into the negative saliva. Chemicals and buffers were obtained from Sigma and Aldrich, Company.

(a) Preparation of Reagents

To determine the presence of amphetamine in saliva, a specific anti-amphetamine monoclonal antibody (available for example, from Omega Biologicals, Inc., Bozeman, Mont.) was coupled to or immobilized on Emphase porous beads according to the manufacturer's standard protocol. The antibody-coupled beads were then saturated with prepared Cy5-labeled amphetamine tracers. The resulting tracer-antibody-resin complex mixture was left overnight at 4° C. while roller mixing. The complex resin was washed with 0.1M PBS (10% MeOH) until a stable baseline was obtained. The washed resin was added to an equal volume of 150 mM trehalose buffer in 50 mM PBS (pH 7.4). The resin was freeze-dried.

(b) Flow Assay

A micro-polystyrene column with an inner diameter of 2 mm and a length of 10 mm was filled with 4 mg of the prepared resin. The filled column was installed into one of the five flow channels of the LifePoint Immunoassay Instrument. The column had been pre-washed with an appropriate buffer controlled by an automatic system supported by Labview software (National Instruments, Inc.). 50 $\mu$l of the saliva sample was passed through the channel at a flow rate of 100 to 300 $\mu$l/minute. The average intensity of the fluorescence signal was used to determine the concentration of amphetamine in the sample.

EXAMPLE IV

Preparation of a Preferred Methamphetamine Immunoassay Tracer

Step 1: Preparation of N-methyl-1-methyl-3-phenylpropylamine-N-trifluoroacetamide:

A solution of 0.4 g of N-methyl-1-methyl-3-phenylpropylamine in 1 ml of acetonitrile was stirred. 1 ml of trifluoroacetic anhydride and 0.6 ml of pyridine was added to the solution at room temperature, and the resulting mixture was stirred overnight at room temperature. Next, the mixture was placed in ice water. The crude product was extracted with ethyl acetate, and the organic layers were combined and dried over $Na_2SO_4$. The desired product was obtained by removal of the organic solvent. TLC analysis ensured that the product was pure enough for the next synthesis step.

Step 2: Preparation of p'-hemisuccinito-N-methyl-1-methyl-3-phenylpropylamine-N-trifluoroacetamide 0.2 g of $AlCl_3$ was added to a mixture of 0.1 g succinic anhydride and 0.2 g N-methyl-1-methyl-3-phenylpropylamine-N-trifluoroacetamide in 5 ml of dichloromethane at room temperature. The resulting mixture was stirred at 2°–8° C. for 1 hour and then left at room temperature overnight. 2 ml of 3M aqueous HCl solution was added to the mixture, and the product was extracted with ethyl acetate. The organic layers were combined and dried over $Na_2SO_4$. The organic solvent was removed to obtain 0.2 g of a crude product. Further purification of the crude product was completed with a silica gel column. Eluting with (1:2) ethyl: hexanes yielded 0.12 g of pure product.

Step 3: Reduction reaction of para-hemisuccinito-N-methyl-1-methyl-3-phenylpropylamine-N-trifluoroacetamide 0.2 g of the prepared of para-hemisuccinito-1-methyl-3-phenylpropylamine-N-trifluoroacetamide was dissolved in 3 ml of acetic acid. 0.3 g of 10% Pd/C was added to the solution. The mixture was hydrogenated under H2 overnight at room temperature. Removal of the catalyst and solvent yielded an oily residue. The resulting mixture was purified by silica TLC using (1/1) ethyl acetate/hexane as developing solvents. 62 mg of the pure product was obtained at the end of this step.

Step 4: Preparation of succinimidyl active ester of para-hemisuccinito-1-methyl-3-phenylpropylamine-N-trifluoroacetamide:

40 mg of para-hemisuccinito-1-methyl-3-phenylpropylamine-N-trifluoroacetamide was stirred into 1 ml of acetonitrile. 40 mg of N,N'-disuccinimidyl carbonate and 60 μl of pyridine was added to the solution. The resulting mixture was stirred at room temperature for 4 hours. Purification of the reaction mixture with a silica plate gave 25 mg of succinimidyl active ester of para-hemisuccinito-1-methyl-3-phenylpropylamine-N-trifluoroacetamide.

Step 5: Coupling of succinimidyl active ester of para-hemisuccinito-1-methyl-3-phenylpropylamine-N-fluoroacetamide with Cy5EDA:

2 mg of succinimidyl active ester of para-hemisuccinito-1-methyl-3-phenylpropylamine-N-fluoroacetamide was mixed with 2.5 mg of CyEDA in 0.5 ml of borate buffer pH 9. The solution was stirred at room temperature for 4 hours, and the resulting solution was directly spotted onto a C18 plate and developed with 70/30-methanol/water. The product band was cut out and the coupled succinimidyl active ester of para-hemisuccinito-1-methyl-3-phenylpropylamine-N-fluoroacetamide with Cy5EDA was extracted with methanol.

EXAMPLE V

Flow Immunoassay of Amphetamine in Saliva a) Preparation of Reagents

Figure 9:
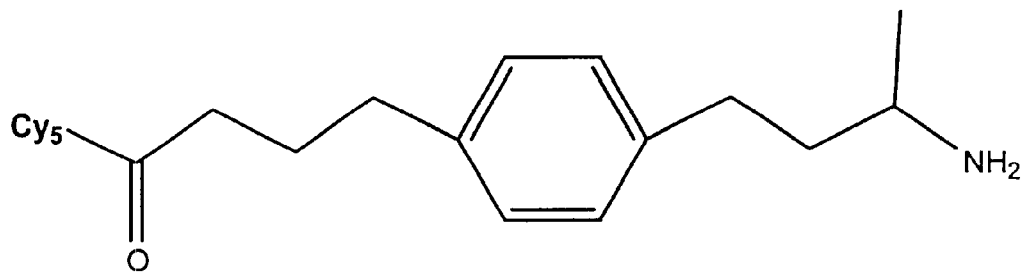
FIG. 9 depicts the preferred synthetic novel tracer compounds which are the reaction product of succinimidyl active ester of para-hemisuccinito-1-methyl-3-phenylpropylamine-N-trifluoroacetamid labeled with Cy5EDA.
Figure 10:
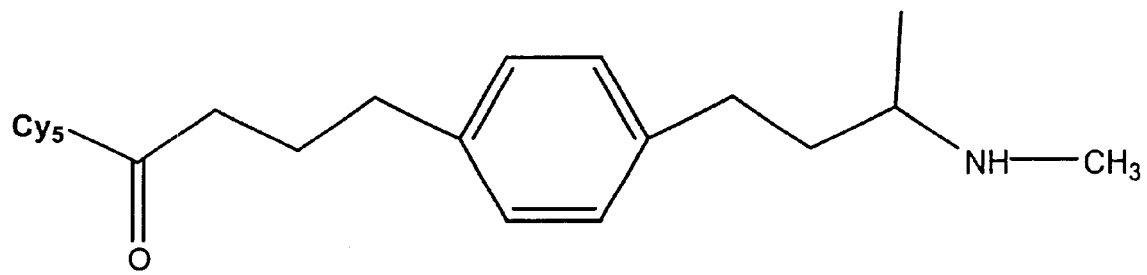
FIG. 10 depicts the preferred synthetic novel tracer compounds which are the reaction product of succinimidyl active ester of para-hemisuccinito-N-methyl-1-methyl 3-phenylpropylamine-N-trifluoroacetamid labeled with Cy5EDA.
Figure 11:
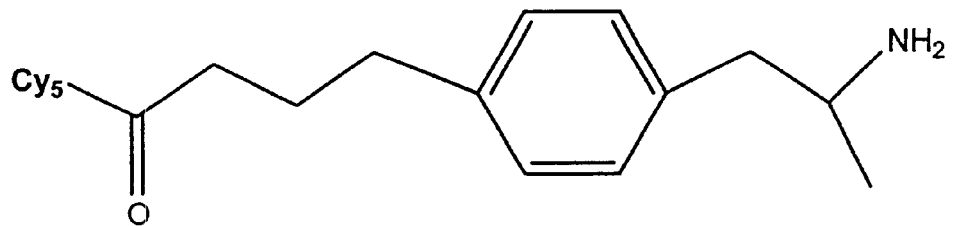
FIG. 11 depicts a conventional (drug based) tracer GW5-12.

The selected anti-amphetamine antibody (available for example, from Omega Biologicals, Inc., Bozeman, Mont.) was coupled to Emphase resin according to the manufacturer's standard procedure and then, saturated with prepared tracers such as GW3-38, a novel tracer of the present invention (FIG. 9) and GW5-12, a conventional tracer (FIG. 11). The resulting complex mixture was allowed to proceed at 4° C. overnight while roller mixing. The complex resin was washed with 0.1M PBS (10% MeOH) until a stable baseline was obtained. The washed resin was added to the same volume of 150 mM trehalose buffer in 50 mM PBS (pH 7.4), and freeze dried.

a) Flow Immunoassay Procedure 4 mg of the prepared resin was filled into a micro-polystyrene column with an inner diameter of 2 mm and a length of 10 mm. The filled column was installed into one of the five flow channels of the LifePoint Immunoassay Instrument. This immunoassay involves pre-washing the column with the appropriate buffer controlled by an automatic system supported by Labview software (National Instruments, Inc.). After that, 50 μl of the test sample was passed through the channel at a flow rate of 100 μl minute and followed by 350 μl of 0.2 % BSA/PBS buffer.

b) Results

The average intensity of the fluorescence signal was used to determine the drug concentration in the sample. The comparison of the flow immunoassay of amphetamine with tracers GW3-38 and GW5-12 is shown in FIGS. 14 and 15. The preferred tracer of the present invention shows almost ten times (10×) the signal intensity as that of the conventional tracer.

What is claimed is:

1. A synthetic tracer for use in an immunoassay for detecting the presence and or quantity of amphetamine and its derivatives in a sample of the formula:

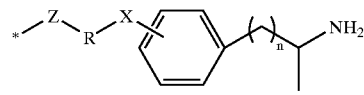

wherein (a) n is a number selected from the group consisting of 2, 3 and 4;
(b) R is selected from the group consisting of —(CH$_2$)n— and C(O)—(CH$_2$)nCO;
(c) X is selected from the group consisting of O, NH, CO, HNCSNH, CH$_2$, S, and SO$_2$;
(d) Z is selected from the group consisting of an amino group or a carboxyl group;
(e) * is a label attached to Z.

2. A synthetic tracer for use in an immunoassay for detecting the presence and or quantity of amphetamine and its derivatives in a sample of the formula:

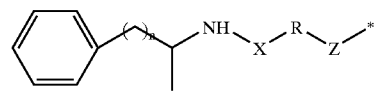

wherein (a) n is a number selected from the group consisting of 2, 3 and 4;
(b) R is selected from the group consisting of —(CH$_2$)n— and C(O)—(CH$_2$)nCO;
(c) X is selected from the group consisting of O, NH, CO, HNCSNH, CH$_2$, S, and SO$_2$;
(d) Z is selected from the group consisting of an amino group or a carboxyl group;
(e) * is a label attached to Z.

3. A synthetic tracer for use in an immunoassay for detecting the presence and or quantity of methamphetamine and its derivatives in a sample of the formula:

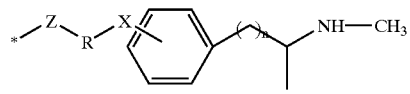

wherein (a) n is a number selected from the group consisting of 2, 3 and 4;
(b) R is selected from the group consisting of —(CH$_2$)n— and C(O)—(CH$_2$)nCO;
(c) X is selected from the group consisting of O, NH, CO, HNCSNH, CH$_2$, S, and SO$_2$;
(d) Z is selected from the group consisting of an amino group or a carboxyl group;
(e) * is a label attached to Z.

4. A synthetic tracer for use in an immunoassay for detecting the presence and or quantity of methamphetamine and its derivatives in a sample of the formula:

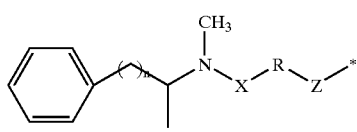

wherein
- (a) n is a number selected from the group consisting of 2, 3 and 4;
- (b) R is a selected from the group consisting of —(CH$_2$)n— and C(O)—(CH$_2$)nCO;
- (c) X is selected from the group consisting of O, NH, CO, HNCSNH, CH$_2$, S, and SO$_2$;
- (d) Z is selected from the group of an amino group or a carboxyl group;
- (e) * is a label attached to Z.

5. A method for determining the presence and or quantity of amphetamine and its derivatives in a sample comprising the steps of:
- (a) providing a solid phase-immobilized antibody to amphetamine,
- (b) exposing an antigen binding site of the antibody to the synthetic tracer of any one of claims 1–4 to form a solid phase-immobilized, labeled synthetic tracer-antibody complex, wherein the antigen binding sites of the antibody are saturated with the labeled synthetic tracers,
- (c) continuously flowing a sample suspected of containing amphetamine past the solid phase-immobilized, labeled antigen-antibody complex under nonequilibrium conditions, and
- (d) detecting the displaced labeled synthetic tracer of any one of claims 1–4, the amount of said displaced labeled synthetic tracer being directly proportional to the concentration of said amphetamine in the sample.

6. The method in accordance with claim 5 wherein the sample is a biological sample.

7. A method in accordance with claim 5 wherein the sample is an aqueous sample.

8. A method in accordance with claim 5 wherein the specific antibody is a monoclonal antibody or polyclonal antibody specific for amphetamines and their derivatives.

9. A synthetic tracer for use in an immunoassay for detecting the presence and or quantity of amphetamine and its derivatives in a sample of the formula:

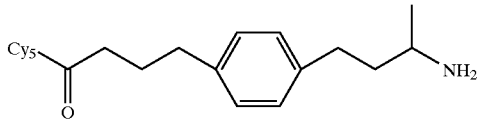

10. A synthetic tracer for use in an immunoassay for detecting the presence and or quantity of amphetamine and its derivatives in a sample of the formula:

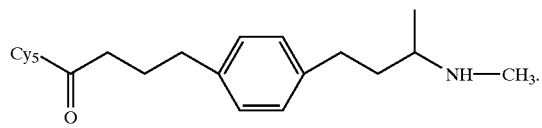

11. The synthetic tracer of claim 1, wherein the label is selected from the group consisting of a fluorophore, a chromophore, a radiolabel, a metal colloid, an enzyme, or a chemiluminescent or bioluminescent molecule.

12. The synthetic tracer of claim 2, wherein the label is selected from the group consisting of a fluorophore, a chromophore, a radiolabel, a metal colloid, an enzyme, or a chemiluminescent or bioluminescent molecule.

13. The synthetic tracer of claim 3, wherein the label is selected from the group consisting of a fluorophore, a chromophore, a radiolabel, a metal colloid, an enzyme, or a chemiluminescent or bioluminescent molecule.

14. The synthetic tracer of claim 4, wherein the label is selected from the group consisting of a fluorophore, a chromophore, a radiolabel, a metal colloid, an enzyme, or a chemiluminescent or bioluminescent molecule.

15. The synthetic tracer of claim 1, wherein the label is a fluorescent dye of the formula:

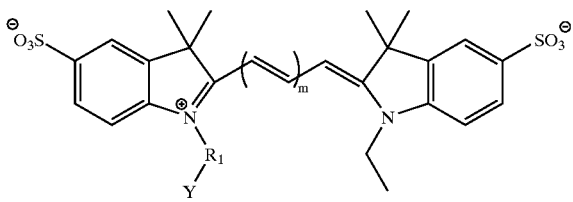

wherein
- (a) m is a number selected from the group consisting of 0, 1, 2, 3 and 4;
- (b) Y is selected from the group consisting of a succinimidyl active ester group (OSu) and an ethylenediamine group (EDA); and
- (c) R$_1$ is selected from the group consisting of —(CH$_2$)n— and C(O)—(CH$_2$)nCO wherein n is a number selected from the group consisting of 2, 3 and 4.

16. The synthetic tracer of claim 2, wherein the label is a fluorescent dye of the formula:

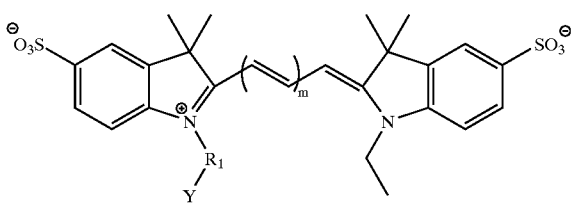

wherein
- (a) m is a number selected from the group consisting of 0, 1, 2, 3 and 4;
- (b) Y is selected from the group consisting of a succinimidyl active ester group (OSu) and an ethylenediamine group (EDA); and
- (c) R$_1$ is selected from the group consisting of —(CH$_2$)n— and C(O)—(CH$_2$)nCO wherein n is a number selected from the group consisting of 2, 3 and 4.

17. The synthetic tracer of claim 3, wherein the label is a fluorescent dye of the formula:

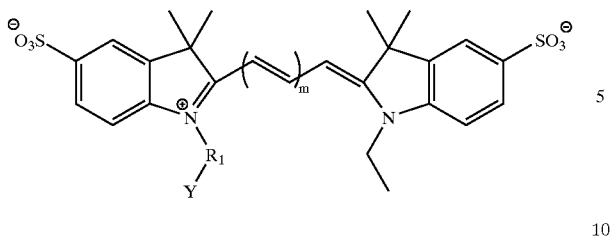

wherein (a) m is a number selected from the group consisting of 0, 1, 2, 3 and 4;

(b) Y is selected from the group consisting of a succinimidyl active ester group (OSu) and an ethylenediamine group (EDA); and (c) $R_1$ is selected from the group consisting of —($CH_2$)n— and C(O)—($CH_2$)nCO wherein n is a number selected from the group consisting of 2, 3 and 4.

18. The synthetic tracer of claim 4, wherein the label is a fluorescent dye of the formula:

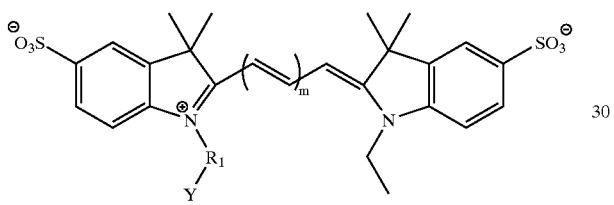

wherein (a) m is a number selected from the group consisting of 0, 1, 2, 3 and 4;

(b) Y is selected from the group consisting of a succinimidyl active ester group (OSu) and an ethylenediamine group (EDA); and (c) $R_1$ is selected from the group consisting of —($CH_2$)n— and C(O)—($CH_2$)nCO wherein n is a number selected from the group consisting of 2, 3 and 4.

19. The synthetic tracer of claim 1, wherein the label is a fluorescent dye of the formula:

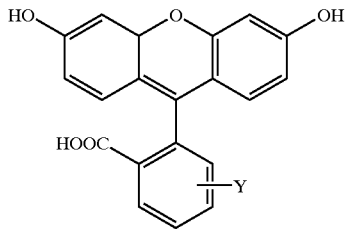

wherein Y is selected from the group consisting of a succinimidyl active ester group (OSu) and an ethylenediamine group (EDA).

20. The synthetic tracer of claim 2, wherein the label is a fluorescent dye of the formula:

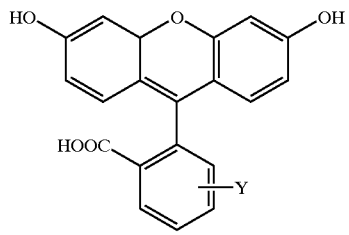

wherein Y is selected from the group consisting of a succinimidyl active ester group (OSu) and an ethylenediamine group (EDA).

21. The synthetic tracer of claim 3, wherein the label is a fluorescent dye of the formula:

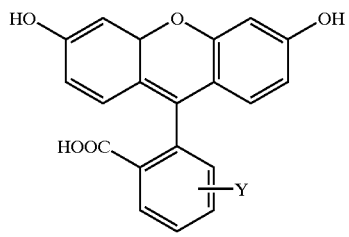

wherein Y is selected from the group consisting of a succinimidyl active ester group (OSu) and an ethylenediamine group (EDA).

22. The synthetic tracer of claim 4, wherein the label is a fluorescent dye of the formula:

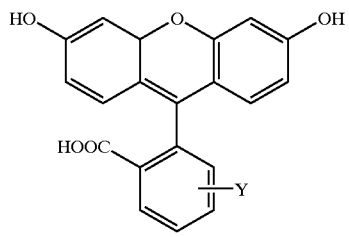

wherein Y is selected from the group consisting of a succinimidyl active ester group (OSu) and an ethylenediamine group (EDA).

23. A synthetic tracer comprising a phenylalkylamine of the formula selected from the group consisting of:

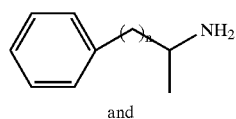

and

attached to a label, wherein n>1.

24. The synthetic tracer of claim 23 wherein n is a number selected from the group consisting of 2, 3, and 4.

25. The synthetic tracer of claim 23, wherein the label is attached to the phenylalkylamine at a position selected from the group consisting of the para-, ortho-, and meta-positions.

26. The synthetic tracer of claim 23 wherein the label is selected from the group consisting of a fluorophore, a chromophore, a radiolabel, a metal colloid, an enzyme, or a chemiluminescent or bioluminescent molecule.

27. The synthetic tracer of claim 23, wherein the label is a fluorescent dye of the formula wherein

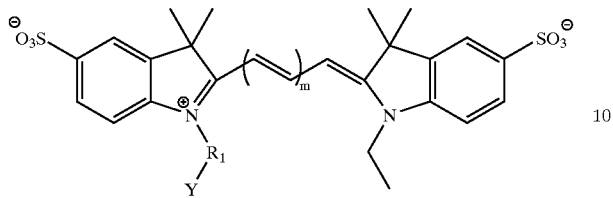

(a) m is a number selected from the group consisting of 0, 1, 2, 3 and 4;
(b) Y is selected from the group consisting of a succinimidyl active ester group (OSu) and an ethylenediamine group (EDA); and
(c) $R_1$ is selected from the group consisting of —(CH$_2$)n— and C(O)—(CH$_2$)nCO wherein n is a number selected from the group consisting of 2, 3 and 4.

28. The synthetic tracer of claim 23, wherein the label is a fluorescent dye of the formula:

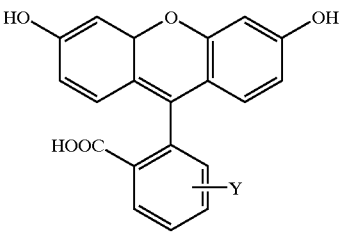

wherein Y is selected from the group consisting of a succinimidyl active ester group (OSu) and an ethylenediamine group (EDA).

* * * * *